(12) United States Patent
Hancock et al.

(10) Patent No.: US 11,980,413 B2
(45) Date of Patent: May 14, 2024

(54) INTERFACE JOINT FOR AN ELECTROSURGICAL APPARATUS

(71) Applicant: CREO MEDICAL LIMITED, Chepstow (GB)

(72) Inventors: Christopher Paul Hancock, Bath (GB); Rohan Monico, Chepstow (GB); Huw Hopkins, Chepstow (GB); Tom Craven, Chepstow (GB); Steve Morris, Chepstow (GB)

(73) Assignee: CREO MEDICAL LIMITED, Monmouth (GB)

( * ) Notice: Subject to any disclaimer, the term of this patent is extended or adjusted under 35 U.S.C. 154(b) by 175 days.

(21) Appl. No.: 17/685,851

(22) Filed: Mar. 3, 2022

(65) Prior Publication Data

US 2022/0183751 A1 Jun. 16, 2022

Related U.S. Application Data

(62) Division of application No. 16/632,826, filed as application No. PCT/EP2018/072154 on Aug. 15, 2018, now abandoned.

(30) Foreign Application Priority Data

Aug. 17, 2017 (GB) ..................................... 1713173

(51) Int. Cl.
*A61B 18/14* (2006.01)
*A61B 18/18* (2006.01)
(Continued)

(52) U.S. Cl.
CPC ...... *A61B 18/1492* (2013.01); *A61B 18/1815* (2013.01); *A61B 2017/0034* (2013.01);
(Continued)

(58) Field of Classification Search
CPC ............ A61B 18/1492; A61B 18/1815; A61B 2017/0034; A61B 2017/00424;
(Continued)

(56) References Cited

U.S. PATENT DOCUMENTS

| 3,783,900 A | 1/1974 | Waldbillig |
| 3,837,345 A | 9/1974 | Matar |

(Continued)

FOREIGN PATENT DOCUMENTS

| CN | 104822331 A | 8/2015 |
| EP | 0 647 122 | 4/1995 |

(Continued)

OTHER PUBLICATIONS

International Search Report and Written Opinion, issued by International Searching Authority in corresponding International Application No. PCT/EP2018/072154, dated Mar. 27, 2019.

(Continued)

*Primary Examiner* — Sean W Collins
(74) *Attorney, Agent, or Firm* — ArentFox Schiff LLP (57) ABSTRACT

An interface joint with one or both of a needle actuation mechanism or an integrated shaft rotation mechanism. The interface joint comprises a flexible shaft between a housing and an electrosurgical instrument, e.g. for conveying power and/or fluid therebetween. The needle actuation mechanism comprises an actuation rod extending out of the housing and an actuator movably mounted on the housing. The shaft rotation mechanism comprises a rotation actuator rotatably mounted on the housing and operably coupled to the flexible shaft. Providing an integrated shaft rotation mechanism may obviate the need for a separate torque transmission unit. The improved needle actuation mechanism may use a pivoting connection to enable longer needle extension distances to be achieved for a given actuation distance.

11 Claims, 6 Drawing Sheets

(51) Int. Cl.
*A61B 17/00* (2006.01)
*A61B 18/00* (2006.01)

(52) U.S. Cl.
CPC ........... *A61B 2017/00424* (2013.01); *A61B 2018/00083* (2013.01); *A61B 2018/00172* (2013.01); *A61B 2018/00178* (2013.01); *A61B 2018/00196* (2013.01); *A61B 2018/00345* (2013.01); *A61B 2018/00601* (2013.01); *A61B 2018/0063* (2013.01); *A61B 2018/00982* (2013.01); *A61B 2018/00994* (2013.01); *A61B 2018/1412* (2013.01); *A61B 2018/1861* (2013.01); *A61B 2218/002* (2013.01)

(58) Field of Classification Search
CPC ........... A61B 2018/00083; A61B 2018/00178; A61B 2018/00345; A61B 2018/00601; A61B 2018/0063; A61B 2018/00982; A61B 2018/00994; A61B 2018/1861; A61B 2218/002; A61B 2018/00172; A61B 2018/00196; A61B 2018/00916; A61B 2018/1412; A61B 2018/1425; A61B 18/1206
See application file for complete search history.

(56) References Cited

U.S. PATENT DOCUMENTS

| | | | |
|---|---|---|---|
| 3,902,498 A | 9/1975 | Niederer | |
| 3,957,082 A | 5/1976 | Fuson et al. | |
| 4,400,168 A | 8/1983 | Buechel et al. | |
| 4,468,216 A | 8/1984 | Muto | |
| 4,516,398 A | 5/1985 | Wuchinich | |
| 4,519,385 A | 5/1985 | Wuchinich | |
| 4,524,770 A | 6/1985 | Orandi | |
| 4,553,957 A | 11/1985 | Williams et al. | |
| 5,019,054 A | 5/1991 | Clement et al. | |
| 5,078,688 A | 1/1992 | Lobodzinski et al. | |
| 5,158,561 A | 10/1992 | Rydell et al. | |
| 5,161,773 A | 11/1992 | Tower | |
| 5,195,959 A | 3/1993 | Smith | |
| 5,197,963 A | 3/1993 | Parins | |
| 5,217,468 A | 6/1993 | Clement | |
| 5,224,929 A | 7/1993 | Remiszewski | |
| 5,242,390 A | 9/1993 | Goldrath | |
| 5,250,065 A | 10/1993 | Clement et al. | |
| 5,273,524 A | 12/1993 | Fox et al. | |
| 5,282,790 A | 2/1994 | Clement | |
| 5,306,237 A | 4/1994 | Clement et al. | |
| 5,312,332 A | 5/1994 | Bales et al. | |
| 5,312,418 A | 5/1994 | Bonnet | |
| 5,335,671 A | 8/1994 | Clement | |
| 5,338,292 A | 8/1994 | Clement et al. | |
| 5,348,555 A | 9/1994 | Zinnanti | |
| 5,350,356 A | 9/1994 | Bales et al. | |
| 5,374,244 A | 12/1994 | Clement et al. | |
| 5,376,094 A | 12/1994 | Kline | |
| 5,391,145 A | 2/1995 | Dorsey, III | |
| 5,499,992 A | 3/1996 | Meade et al. | |
| 5,542,915 A * | 8/1996 | Edwards | A61B 10/06 604/22 |
| 5,609,573 A | 3/1997 | Sandock | |
| 5,626,607 A | 5/1997 | Malecki et al. | |
| 5,647,871 A | 7/1997 | Levine et al. | |
| 5,685,877 A | 11/1997 | Pagedas | |
| 5,797,960 A | 8/1998 | Stevens et al. | |
| 5,873,855 A | 2/1999 | Eggers et al. | |
| 6,123,665 A | 9/2000 | Kawano et al. | |
| 6,193,672 B1 | 2/2001 | Clement et al. | |
| 6,346,107 B1 | 2/2002 | Cucin | |
| 6,620,161 B2 | 9/2003 | Schulze et al. | |
| 7,101,362 B2 | 9/2006 | Vanney | |
| 7,731,716 B1 | 6/2010 | Christoudias | |
| 8,721,595 B2 | 5/2014 | Stiehl et al. | |
| 8,777,943 B2 | 7/2014 | Mayse et al. | |
| 10,610,284 B2 | 4/2020 | Hancock et al. | |
| 11,090,116 B2 | 8/2021 | Hancock et al. | |
| 2001/0025177 A1 | 9/2001 | Woloszko et al. | |
| 2002/0062123 A1 | 5/2002 | Mcclurken et al. | |
| 2002/0087156 A1 | 7/2002 | Maguire et al. | |
| 2003/0040657 A1 | 2/2003 | Yamaya et al. | |
| 2003/0229344 A1 | 12/2003 | Dycus et al. | |
| 2004/0215181 A1 | 10/2004 | Christopherson et al. | |
| 2005/0131399 A1 | 6/2005 | Loeb et al. | |
| 2006/0036235 A1 | 2/2006 | Swoyer et al. | |
| 2006/0241655 A1 | 10/2006 | Viola et al. | |
| 2007/0233059 A1 | 10/2007 | Christoudias et al. | |
| 2007/0250051 A1 | 10/2007 | Gaston et al. | |
| 2008/0262491 A1 | 10/2008 | Swoyer et al. | |
| 2008/0269862 A1 | 10/2008 | Elmouelhi et al. | |
| 2009/0030414 A1 | 1/2009 | Bayat | |
| 2010/0030262 A1 | 2/2010 | McLean et al. | |
| 2010/0179546 A1 | 7/2010 | Cunningham | |
| 2010/0217151 A1 | 8/2010 | Gostout et al. | |
| 2011/0060349 A1 | 3/2011 | Cheng et al. | |
| 2011/0118724 A1 | 5/2011 | Turner et al. | |
| 2011/0306972 A1 | 12/2011 | Widenhouse et al. | |
| 2012/0165809 A1 | 6/2012 | Christian et al. | |
| 2013/0172784 A1 | 7/2013 | Kirschenman | |
| 2013/0211379 A1 | 8/2013 | Clair et al. | |
| 2015/0209101 A1 | 7/2015 | Mark et al. | |
| 2015/0313666 A1 | 11/2015 | Aljuri et al. | |
| 2016/0235468 A1 | 8/2016 | Prisco et al. | |
| 2016/0324576 A1 * | 11/2016 | Ebbutt | A61B 18/1815 |
| 2017/0014638 A1 | 1/2017 | Preston et al. | |
| 2017/0050041 A1 | 2/2017 | Cosman | |
| 2017/0224411 A1 | 8/2017 | Onuki et al. | |
| 2022/0000554 A1 | 1/2022 | Hancock et al. | |

FOREIGN PATENT DOCUMENTS

| | | |
|---|---|---|
| EP | 2617379 A1 | 7/2013 |
| JP | 2001-79017 A | 3/2001 |
| WO | WO2015/101787 A2 | 7/2015 |
| WO | WO-2015101787 A2 * | 7/2015 ........... A61B 18/042 |

OTHER PUBLICATIONS

Search Report under Section 17(5), issued by the United Kingdom Intellectual Property Office in counterpart United Kingdom Application No. GB1713173.1, dated Feb. 15, 2018.

* cited by examiner

INTERFACE JOINT FOR AN ELECTROSURGICAL APPARATUS

CROSS-REFERENCE TO RELATED APPLICATIONS

This application is a Divisional of U.S. patent application Ser. No. 16/632,826, filed on Jan. 21, 2020, which is a U.S. National Stage application of PCT International Application No. PCT/EP2018/072154, filed Aug. 15, 2018, which claims priority to United Kingdom Patent Application No. 1713173.1, filed Aug. 17, 2017. The disclosures of the prior applications are incorporated herein by reference in their entireties.

FIELD OF THE INVENTION

The invention relates to an electrosurgical apparatus in which an electrosurgical instrument is inserted through the instrument channel of a surgical scoping device in order to treat biological tissue located beyond a distal end of the instrument channel. In particular, the invention relates to a control device, e.g. a handle, that is located outside the surgical scoping device and used to manipulate or otherwise operate the electrosurgical instrument.

BACKGROUND TO THE INVENTION

Surgical resection is a means of removing sections of organs from within the human or animal body. Such organs may be highly vascular. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting. For endoscopic procedures, it is also undesirable for a bleed to occur and not to be dealt with as soon as quickly as possible, or in an expedient manner, since the blood flow may obscure the operator's vision, which may lead to the procedure needing to be terminated and another method used instead, e.g. open surgery.

Electrosurgical generators are pervasive throughout hospital operating theatres, for use in open and laparoscopic procedures, and are also increasingly present in endoscopy suites. In endoscopic procedures the electrosurgical accessory is typically inserted through a lumen inside an endoscope. Considered against the equivalent access channel for laparoscopic surgery, such a lumen is comparatively narrow in bore and greater in length. In the case of a bariatric patient the surgical accessory may have a length of 300 mm from handle to RF tip, whereas the equivalent distance in a laparoscopic case can be in excess of 2500 mm.

Instead of a sharp blade, it is known to use radiofrequency (RF) energy to cut biological tissue. The method of cutting using RF energy operates using the principle that as an electric current passes through a tissue matrix (aided by the ionic contents of the cells and the intercellular electrolytes), the impedance to the flow of electrons across the tissue generates heat. When an RF voltage is applied to the tissue matrix, enough heat is generated within the cells to vaporise the water content of the tissue. As a result of this increasing desiccation, particularly adjacent to the RF emitting region of the instrument (referred to herein as an RF blade) which has the highest current density of the entire current path through tissue, the tissue adjacent to the cut pole of the RF blade loses direct contact with the blade. The applied voltage is then appears almost entirely across this void which ionises as a result, forming a plasma, which has a very high volume resistivity compared to tissue. This differentiation is important as it focusses the applied energy to the plasma that completed the electrical circuit between the cut pole of the RF blade and the tissue. Any volatile material entering the plasma slowly enough is vaporised and the perception is therefore of a tissue dissecting plasma.

GB 2 523 246 describes an electrosurgical instrument for applying to biological tissue RF electromagnetic energy and/or microwave frequency EM energy. The instrument comprises a shaft insertable through an instrument channel of a surgical scoping device. At a distal end of the shaft there is an instrument tip comprising a planar transmission line formed from a sheet of a first dielectric material having first and second conductive layers on opposite surfaces thereof. The planar transmission line is connected to a coaxial cable conveyed by the shaft. The coaxial cable is arranged to deliver either microwave or RF energy to the planar transmission line. The coaxial cable comprises an inner conductor, an outer conductor coaxial with the inner conductor, and a second dielectric material separating the outer and inner conductors, the inner and outer conductors extending beyond the second dielectric at a connection interface to overlap opposite surfaces of the transmission line and electrically contact the first conductive layer and second conductive layer respectively. The instrument further comprises a protective hull with a smoothly contoured convex undersurface facing away from the planar transmission line. The undersurface comprises a longitudinally extending recessed channel formed therein. A retractable needle is mounted within the instrument, and operable to extend through the recessed channel to protrude from a distal end of the instrument. The needle can be used to inject fluid into a treatment zone before the RF or microwave energy is applied.

GB 2 523 246 further discloses a hand-held interface joint at a proximal end of the shaft. The interface joint integrates into the shaft all of (i) a fluid feed, (ii) a needle movement mechanism, and (iii) an energy feed (e.g. a coaxial cable). The interface joint includes a slider mechanism for operating the retractable needle.

SUMMARY OF THE INVENTION

At its most general, the present invention provides an interface joint with one or both of an improved needle actuation mechanism or an integrated shaft rotation mechanism. Providing an integrated shaft rotation mechanism may obviate the need for a separate torque transmission unit. The improved needle actuation mechanism may use a pivoting connection to enable longer needle extension distances to be achieved for a given actuation distance.

According to a first aspect of the invention, there is provided an interface joint for interconnecting an electrosurgical generator and an electrosurgical instrument, the interface joint comprising: a housing made of electrically insulating material, the housing having: a first inlet for receiving radiofrequency (RF) electromagnetic (EM) energy and/or microwave frequency EM energy from the electrosurgical generator, a second inlet for receiving fluid, and an outlet; a flexible shaft for connecting the housing to the electrosurgical instrument, the flexible shaft extending through the outlet and having a longitudinal passage therein, which provides a fluid flow path that is in fluid communication with the second inlet, and which conveys a coaxial transmission line that is connected to the first inlet; an actuation mechanism operably connected to the electrosurgical instrument to control deployment of a fluid delivery structure, the actuation mechanism comprising: an actuation rod extending out of the housing through the outlet, an actuator movably mounted on the housing and connected to the actuation rod; and a shaft rotation mechanism for rotating the flexible shaft relative to the housing, the shaft rotation mechanism comprising a rotation actuator rotatably mounted on the housing and operably coupled to the flexible shaft. In this aspect, the interface joint not only combines together the fluid supply and power feed for the electrosurgical instrument, but it also provides both a linear actuation mechanism (e.g. to deploy the fluid delivery structure within the instrument) and a rotation actuation mechanism that can drive rotation of the shaft and therefore the instrument.

The electrosurgical generator may be any device capable of delivery RF EM energy or microwave frequency EM energy for treatment of biological tissue. For example, the generator described in WO 2012/076844 may be used.

The electrosurgical instrument may be any device which in use is arranged to use RF EM energy or microwave frequency EM energy for the treatment of biological tissue. The electrosurgical instrument may use the RF EM energy and/or microwave frequency EM energy for any or all of resection, coagulation and ablation. For example, the instrument may be a resection device such as that disclosed in WO2015/101787, but alternatively may be any of a pair of microwave forceps, a snare that radiates microwave energy and/or couples RF energy, and an argon beam coagulator.

The housing may provide a double isolation barrier for the operator, i.e. the housing may comprise an outer casing (first level of isolation) that encapsulates a branched passageway (second level of isolation) within which the various inputs are integrated into the flexible shaft, which may provide a single cable assembly. The branched passageway may provide a watertight volume which defines a fluid flow path between the second inlet and the outlet, and which has a first port adjacent to the first inlet for admitting the coaxial cable. The actuation rod may extend through the same structure, i.e. the branched conduit may have a second port adjacent the actuation mechanism for admitting the actuation rod. The actuation rod may be conveyed through longitudinal passage of the flexible shaft, e.g. alongside the coaxial transmission line.

In use, the interface joint may be the location at which fluid for treatment at the instrument is introduced. The operator of the interface joint may control the introduction of fluid, e.g. via a syringe or other fluid introducing mechanism attached to the second inlet. The actuation mechanism may comprise a slider element mounted on the housing, the slider element being attached to the actuation rod that extends out of the housing through the outlet. Other types of actuation mechanism may also be used, e.g. the pivoting mechanism discussed below, or a rack type mechanism operating by a rotating wheel. The fluid delivery structure may comprise a retractable needle at the electrosurgical instrument (i.e. at a distal end of the flexible shaft). The retractable needle may be switchable into and out of fluid communication with the fluid flow path in the flexible shaft by sliding the actuation rod back and forth. For example, a distal end of the actuation rod may be connected to a proximal end of a needle ferrule, which has an internal volume in fluid communication with the fluid flow path through the flexible shaft. The needle may be mounted at a distal end of the needle ferrule, and arranged to be in fluid communication with the internal volume.

The rotation actuator may comprise a collar mounted around a distal portion of the housing. The rotation actuator is rotatable relative to the housing around an axis that is aligned with a direction in which the flexible shaft passes through the outlet. The rotation actuator and the housing may have interengaging elements arranged to provide feedback for a user. For example, the rotation actuator may click as it is rotated. The clicks may increase in frequency or volume as the amount of rotation from a centred position is increased.

The rotation actuator may be integrated with one or more elements that form the fluid flow path. For example, the housing may include an internal watertight branched conduit that provides a fluid flow path between the second inlet and the outlet. The branched conduit may comprise a main conduit fixed to the housing, and a rotating luer lock fitting rotatably mounted to a distal end of the main conduit. The flexible shaft may be non-rotatably coupled (e.g. adhered or otherwise affixed) to the rotating luer lock fitting, while the rotation actuator is connected to rotate the rotating luer lock fitting relative to the main conduit.

A second aspect of the invention provides an interface joint for interconnecting an electrosurgical generator and an electrosurgical instrument, the interface joint comprising: a housing made of electrically insulating material, the housing having: a first inlet for receiving radiofrequency (RF) electromagnetic (EM) energy and/or microwave frequency EM energy from the electrosurgical generator, a second inlet for receiving fluid, and an outlet; a flexible shaft for connecting the housing to the electrosurgical instrument, the flexible shaft extending through the outlet and having a longitudinal passage therein, which provides a fluid flow path that is in fluid communication with the second inlet, and which conveys a coaxial transmission line that is connected to the first inlet; an actuation mechanism operably connected to the electrosurgical instrument to control deployment of a fluid delivery structure, the actuation mechanism comprising: an actuation rod extending out of the housing through the outlet, an actuator arm pivotably mounted on the housing, the actuator arm having a first portion that protrudes from the housing, and a second portion operably connected to the actuation rod. Any features of the first aspect may be combined with the second aspect. In other words, the actuation mechanism of the second aspect may be incorporated into an interface joint having a shaft rotation mechanism.

The actuation mechanism may comprise a guide element slidably mounted in a reciprocal manner with respect to the housing. The guide element may be connected to a proximal end of the actuation rod, and the second portion of the actuator arm may be connected to the guide element by a drive arm. The guide element, drive arm and actuator arm may form an articulated structure that converts pivoting motion into longitudinal motion. The housing may comprise a track integrally formed therein for constraining the guide element to be movable only in a longitudinal direction. The longitudinal direction may be aligned with a direction in which the flexible shaft passes through the outlet.

The actuator arm may be connected to the housing at a pivot point, and wherein the second portion is further from the pivot point than the first portion. This may enable the device to drive the actuation rod for a distance that is longer than the distance travelled by the actuation arm. In other words a given movement of a user's finger can be transformed into a longer movement in the fluid delivery structure.

As discussed the housing includes an internal watertight branched conduit that provides a fluid flow path between the second inlet and the outlet. The branched conduit may have a first port adjacent to the first inlet for admitting the coaxial cable, and a second port adjacent the actuation mechanism for admitting the actuation rod. Both the first port and the second port may comprise a plug or sealing bung which defines a watertight passage for the coaxial cable and the actuation rod respectively. Each plug may be formed from a resiliently deformable material, e.g. silicone rubber, whereby the coaxial cable and push rod are encapsulated in the material as they pass through it. Sealing the first and second ports in this way means that the only route for fluid out of the interface joint is through the outlet along the fluid flow path in the flexible shaft.

In either of the aspects discussed above, a connector (e.g. a QMA connector) may be rotatably mounted at the first inlet, wherein the connector is arranged to connect to a coaxial cable from the electrosurgical generator. In one example, the connector may be mounted within a bearing unit that is fixed to the housing. The connector may be secured within an inner race of a ball bearing, with the outer race being fixed to the housing. This may enable the connector to be freely rotatable with respect to the housing.

In order to facilitate manipulation of the instrument at the distal end of the instrument channel of the endoscope, the flexible sheath may be provided with longitudinal braids therein to assist in the transfer of torque, i.e. to transfer a twisting motion at the proximal end of the cable assembly to the distal end of the cable assembly, where it can cause bi-rotational rotation of the instrument because the instrument is attached to the cable assembly. The flexible sheath may comprises a inner tube and an outer tube, which are bonded or otherwise attached together with a tube of metallised braiding in between. The pitch of the braiding may be variable along the length of the cable assembly. For example, it may be useful to have a wider pitch in a region e.g. a distal portion of the cable, where flexibility is important. In order to prevent the metallised braiding from interfering with the RF field or microwave field at the instrument, a distal portion of the flexible sheath may be provided in which the braided is absent. The distal portion may be manufactured separately and attached (e.g. bonded or welded) to the braided portion.

The housing may further comprise a strain relief element mounted in the outlet and surrounding the flexible shaft. The function of the strain relief element is to limit the movement of the sleeve in this location to prevent overflexing that may damage the internal components.

The term "surgical scoping device" may be used herein to mean any surgical device provided with an insertion tube that is a rigid or flexible (e.g. steerable) conduit that is introduced into a patient's body during an invasive procedure. The insertion tube may include the instrument channel and an optical channel (e.g. for transmitting light to illuminate and/or capture images of a treatment site at the distal end of the insertion tube. The instrument channel may have a diameter suitable for receiving invasive surgical tools. The diameter of the instrument channel may be 5 mm or less.

Herein, the term "inner" means radially closer to the centre (e.g. axis) of the instrument channel and/or coaxial cable. The term "outer" means radially further from the centre (axis) of the instrument channel and/or coaxial cable.

The term "conductive" is used herein to mean electrically conductive, unless the context dictates otherwise.

Herein, the terms "proximal" and "distal" refer to the ends of the elongate probe. In use the proximal end is closer to a generator for providing the RF and/or microwave energy, whereas the distal end is further from the generator.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. In contrast, this specification uses "radiofrequency" or "RF" to indicate a frequency range that is at least three orders of magnitude lower, e.g. up to 300 MHz, preferably 10 kHz to 1 MHz, and most preferably 400 kHz.

The electrosurgical instrument discussed herein may be capable of delivering radiofrequency (RF) electromagnetic (EM) energy and/or microwave EM energy into biological tissue. In particular, the electrosurgical instrument may be capable of delivering radiofrequency (RF) energy for cutting tissue and/or microwave frequency energy for haemostasis (i.e. sealing broken blood vessels by promoting blood coagulation). The invention may be particularly suitable in gastrointestinal (GI) procedures associated with the lower and upper GI tract, e.g. to remove polyps on the bowel, i.e. for endoscopic submucosal resection. The invention may also lend itself to precision endoscopic procedures, i.e. precision endoscopic resection, and may be used in ear, nose and throat procedures and liver resection. The device may also be used to address procedures associated with the pancreas, e.g. to resect or remove tumours or abnormalities in close proximity to the portal vein or the pancreatic duct.

BRIEF DESCRIPTION OF THE DRAWINGS

Embodiments of the invention are described in detail below with reference to the accompanying drawings, in which.

DETAILED DESCRIPTION; FURTHER OPTIONS AND PREFERENCES

Various aspects of the present inventions are presented below in the context of an electrosurgery system that provides an electrosurgical invasive instrument for use in endoscopic procedures for the removal of polyps and malignant growths through the controlled delivery of both microwave and RF energy. However, it is to be understood that the aspects of the invention presented herein need not be limited to this particular application. They may be equally applicable in embodiments where only RF energy is required, or where only RF energy and fluid delivery is required.

Figure 1:
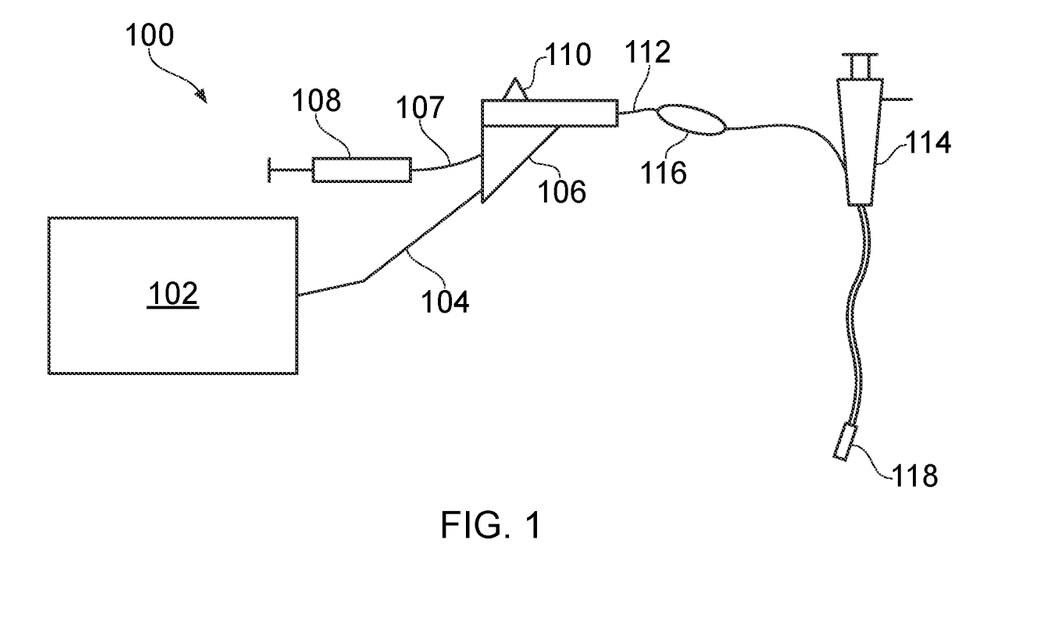
FIG. 1 is a schematic diagram of an electrosurgery system with which the present invention may be used.

FIG. 1 is a schematic diagram of a complete electrosurgery system 100 that is capable of selectively supplying to the distal end of an invasive electrosurgical instrument any or all of RF energy, microwave energy and fluid, e.g. saline or hyaluronic acid. The system 100 comprises a generator 102 for controllable supplying RF electromagnetic (EM) energy and/or microwave frequency EM energy. A suitable generator for this purpose is described in WO 2012/076844, which is incorporated herein by reference.

The generator 102 is connected to an interface joint 106 by an interface cable 104. The interface joint 106 is also connected to receive a fluid supply 107 from a fluid delivery device 108, such as a syringe. The interface joint 106 houses a needle movement mechanism that is operable using an actuator 110. The function of the interface joint 106 is to combine the inputs from the generator 102, fluid delivery device 108 and needle movement mechanism into a single flexible shaft 112, which extends from the distal end of the interface joint 106. Examples of interface joints (which may be referred to herein as a "handle" or "handpiece" or "control device") that are embodiments of the invention are discussed in more detail below.

The flexible shaft 112 is insertable through the entire length of an instrument (working) channel of a surgical scoping device 114. The surgical scoping device 114 may be an endoscope, gastroscope, bronchoscope, or the like. The instrument channel may extend though an instrument cord of the surgical scoping device, which is steerable in a conventional manner. The surgical scoping device 114 may include an optical channel for providing images of a treatment zone at a distal end of the instrument cord.

A torque transfer unit 116 may be mounted on a proximal length of the shaft 112 between the interface joint 106 and endoscope 114. The torque transfer unit 116 engages the shaft to permit it to be rotated within the instrument channel of the endoscope 114. As discussed below, in one embodiment of the invention, the torque transfer unit is incorporated into the interface joint 106.

The flexible shaft 112 has a distal assembly 118 that is shaped to pass through the instrument channel of the endoscope 114 and protrude (e.g. inside the patient) at the distal end of the instrument cord. The distal end assembly includes an active tip for delivering RF EM energy and/or microwave EM energy into biological tissue and a retractable hypodermic needle for delivering fluid. These combined technologies provide a unique solution for cutting and destroying unwanted tissue and the ability to seal blood vessels around the targeted area. Through use of the retractable hypodermic needle, the surgeon is able to inject saline and/or hyaluronic acid with added marker dye between tissues layers in order to distend and mark the position of a lesion to be treated. The injection of fluid in this manner lifts and separates the tissue layers making it both easier to resect around the lesion and plane through the submucosal layer, reducing the risk of bowel wall perforation and unnecessary thermal damage to the muscle layer.

At the proximal end of the instrument channel, which is typically held 50 cm to 80 cm from the patient, the flexible shaft 112 emerges from a port and extends a further 30 cm to 100 cm to the interface joint 106. In use, the interface joint 106 is typically held by a gloved assistant throughout the procedure. The interface joint 106 may be designed and manufactured from polymer materials in such a way as to provide primary and secondary electrical insulation with extended creepage and clearance distances.

Figure 2:
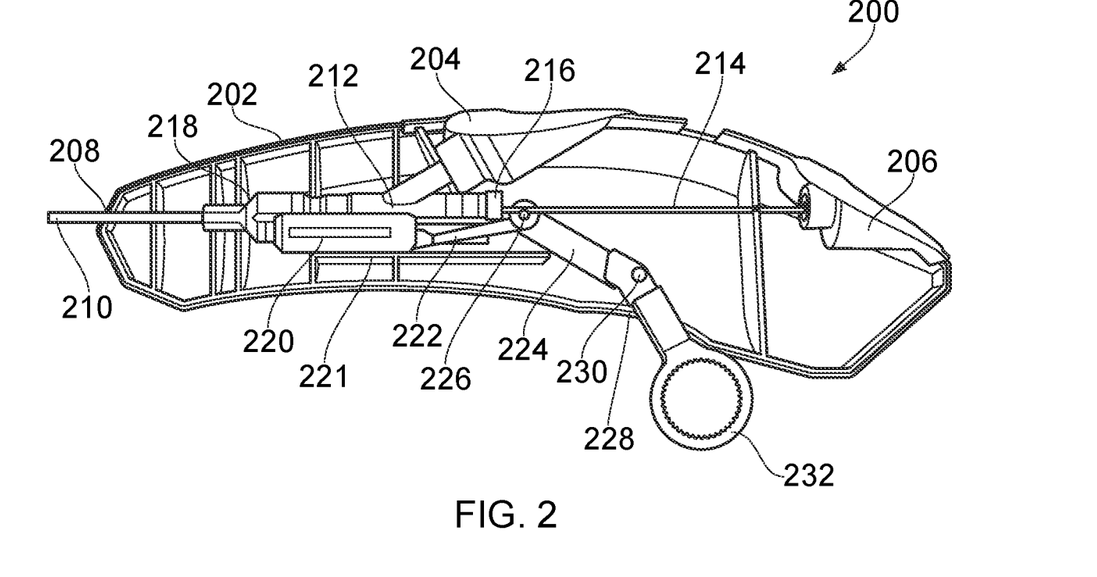
FIG. 2 is a cross-sectional view through an interface joint for an electrosurgical apparatus that is a first embodiment of the invention, with a needle actuation mechanism in a extended position.
Figure 3:
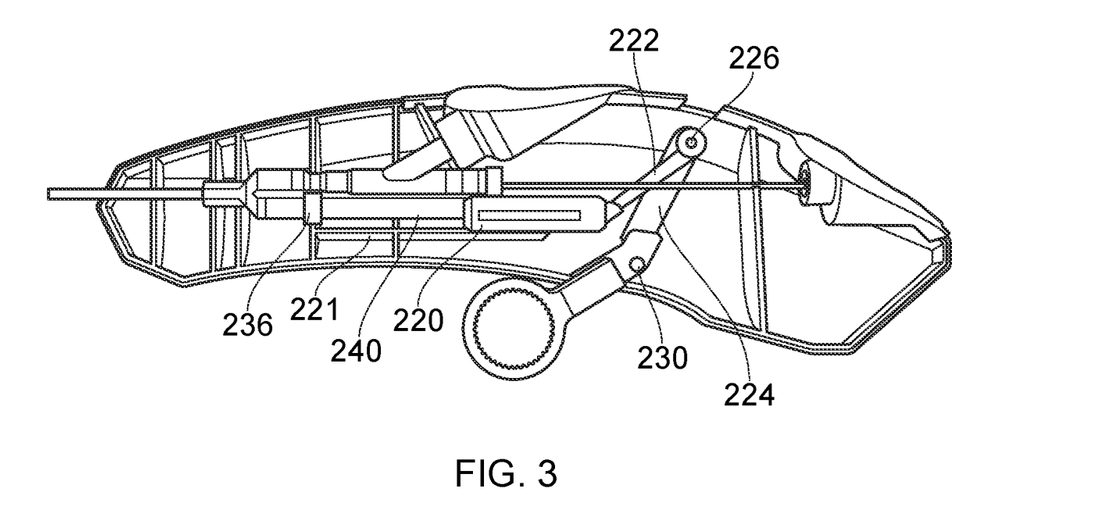
FIG. 3 is a cross-sectional view through the interface joint of FIG. 2, with the needle actuation mechanism in a retracted position.
Figure 4:
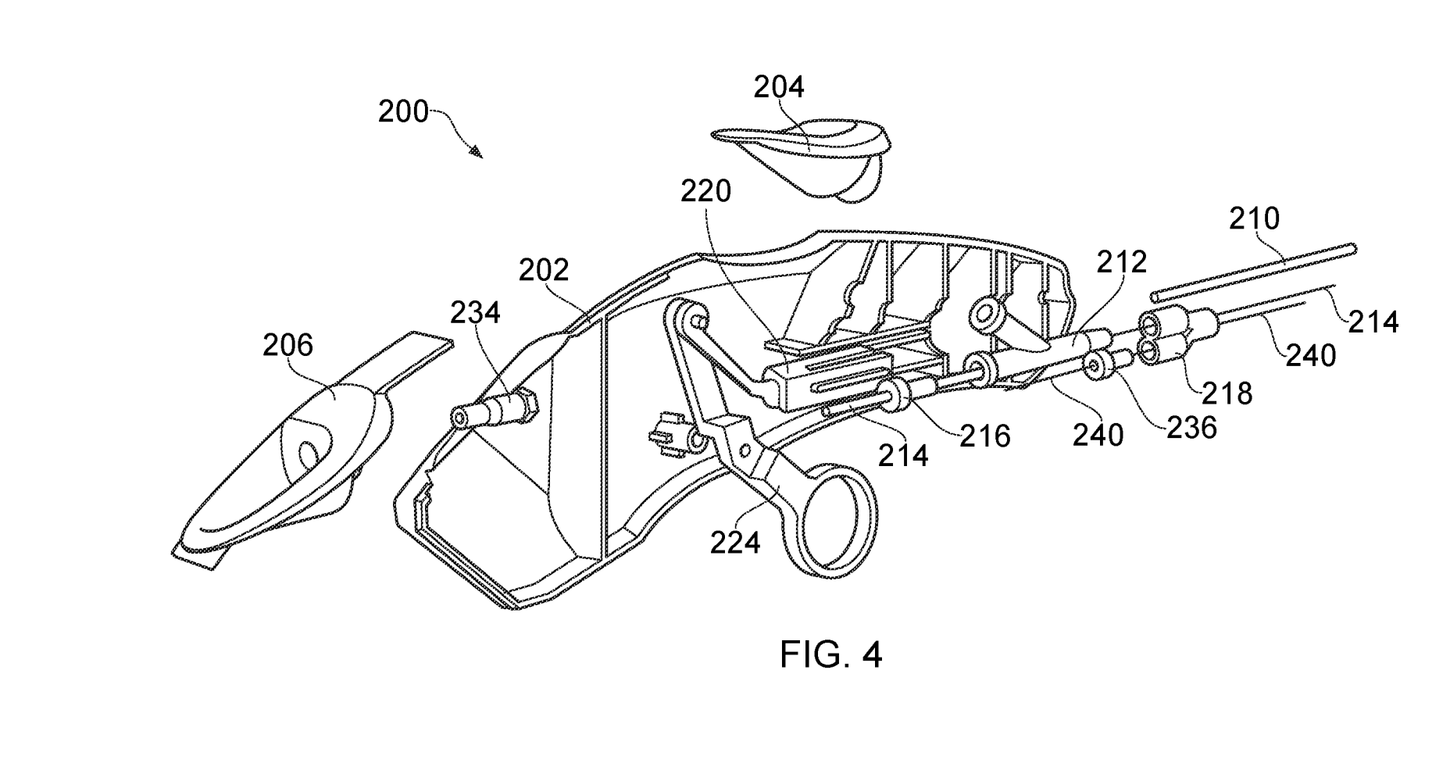
FIG. 4 is a cut-away exploded rear perspective view of the interface joint of FIG. 2.

FIGS. 2, 3 and 4 show various views of an interface joint 200 that is a first embodiment of the invention. The interface joint 200 may be used with the apparatus 100 discussed above, in place of the interface joint 106.

The interface joint 200 comprises a housing 202, e.g. formed from a rigid polymer. The housing 202 encasing the components of the interface joint 200 discussed below.

The housing 202 has a plurality of apertures in its outer surface which provide various ports for the joint.

On a top surface there is a first port for receiving a fluid supply, e.g. a syringe for injecting a liquid such as saline or hyaluronic acid. The first port has a moulded receiving element 204 mounted therein. The moulded receiving element 204 may be shaped to cooperate with a connection interface of the fluid supply to provide a secure interconnection.

At the rear (proximal end) of the housing there is a second port for receiving power from the electrosurgical generator. The second port may include a QMA connector 234 or the like (see FIG. 4) that can couple a coaxial cable from the electrosurgical generator to a coaxial transmission line 214 within the housing 202. The second port has a moulded connection element 206 mounted therein. The moulded connection element 206 may be shaped to cooperate with the QMA connector and/or the coaxial cable from the electrosurgical generator to provide a secure interconnection.

At the front (distal end) of the housing 202 there is a third port 208 from which a flexible shaft 210 extends. The flexible shaft 210 comprise a sheath defining a longitudinal passageway for conveying the fluid from the first port, the coaxial cable 214 from the second port, and a needle actuation rod 240 (see FIG. 4) to an electrosurgical instrument at a distal end thereof.

On the bottom of the housing 202 there is a fourth port 228 through which an actuator for a needle actuation mechanism protrudes. The needle actuation mechanism is discussed in more detail below.

Within the housing 202, a pair of Y conduit connectors 212, 218 are provided to define respective pathways for (i) the fluid from the first port, (ii) the coaxial transmission line 214 from the second port, and (iii) the needle actuation rod 240 associated with the needle actuation mechanism to the flexible shaft 210. The Y conduit connecters 212, 218 are retained in the housing 202, e.g. by being clipped within ribs or other projections that are integrally formed in the housing.

A first Y conduit connector 212 has a first input tube connected to the moulded receiving element 204 in a fluid tight manner, and a second input tube arranged to receive the coaxial transmission line 214 from the second port. A plug 216 is mounted at the proximal end of the second input tube. The coaxial transmission line 214 passes through the plug 216. The plug 216 is formed from resilient material so that it defines a fluid tight seal around the coaxial transmission line 214. The first Y conduit connector 212 has an output tube connected to a first input tube of a second Y conduit connector 218. The fluid and coaxial transmission line 214 are thus conveyed together to the second Y conduit connector 218.

The second Y conduit connector 218 comprises a second input tube connected to receive the needle actuation rod 240. The needle actuation rod 240 is slidable under operation of the needle actuation mechanism into and out of the second Y conduit connector. A plug 236 is secured at the proximal end of the second input tube of the second Y conduit connector to prevent fluid from leaking. The plug 236 is formed from resilient material so that it defines a fluid tight seal around the needle actuation rod 240 whilst still permitting slidable movement thereof.

The second Y conduit connector 218 comprises an output tube that is secured to a proximal end of the flexible shaft 210 in a fluid tight manner, whereby all of (i) the fluid from the first port, (ii) the coaxial transmission line 214 from the second port, and (iii) the needle actuation rod 240 are transferred into a longitudinal passageway defined within the flexible shaft 210.

As shown in FIG. 4, in this example the first Y conduit connector has the first and second input tubes at an acute angle to each other, whereas the second Y conduit connector has its first and second input tubes in parallel. However, the invention is not limited to this arrangement. In other embodiments different junctions may be used. For example, a single junction with three input tubes leading to a single output tube may be used.

The needle actuation mechanism will now be discussed in more detail. FIG. 2 shows the interface joint when the needle is extended. FIG. 3 shows the interface joint when the needle is retracted. The needle itself is located in the electrosurgical instrument at a distal end of the flexible shaft 210. It is connected to a distal end of the needle actuation mechanism by the needle actuation rod 240, which is slidable with the shaft 210. A proximal end of the needle actuation rod 240 is connected to a guide element 220, which is slidably mounted in a track 221 defined by projecting ribs within the housing 202. The track 221 extends in a longitudinal direction, i.e. a direction in line with a direction in which the flexible shaft 210 extends away from the housing 202. Movement of the guide element 220 along the track 221 therefore controls movement of the needle actuation rod 240 into and out of the flexible shaft 210.

In FIG. 2, the guide element 220 is at a distal end of the track 221, whereby the needle actuation rod 240 is fully extended into the flexible shaft 210. In FIG. 3, the guide element 220 is at a proximal end of the track 221, whereby the needle actuation rod 240 is at a retracted position relative to the flexible shaft 210.

Movement of the guide element 220 is controlled by a pivoting trigger mechanism. The trigger mechanism comprises a trigger arm 224 which is pivotably connected to the housing 202 via a pin 230, which defines a first pivot axis. The trigger arm 224 extends out of the fourth port 228 and terminates at a first end in a finger grip 232. The finger grip 232 is arranged to facilitate operation (i.e. forwards and backwards motion) of the trigger arm 224 by a user holding the housing 202. In this example, the finger grip 232 is a ring for receiving a user's finger.

A second end of the trigger arm 224 is connected to a drive arm 222 via a hinge 226. The drive arm 222 in turn is pivotably connected to the guide element 220 so that its angle relative to the guide element 220 can change as the guide element 220 slides along the track 221. The hinge 226 defines a second pivot axis that moves within the housing 202 when the trigger arm 224 is operated.

By providing an articulated needle actuation mechanism it may be possible to provide an increased distance of travel for the needle actuation rod 240 for a given movement of the finger grip 232 through suitable positioning of the pivot points. This can be advantageous compared with actuation mechanisms in which the rod is moved by a liner slider without any gearing.

The location of the first port and second port on the interface joint 200 are arranged such that a user can grip and hold the device with their hand between the fluid supply and the power supply. The spacing between these ports may be desirable to assist in assembly and to avoid any interference.

Figure 5:
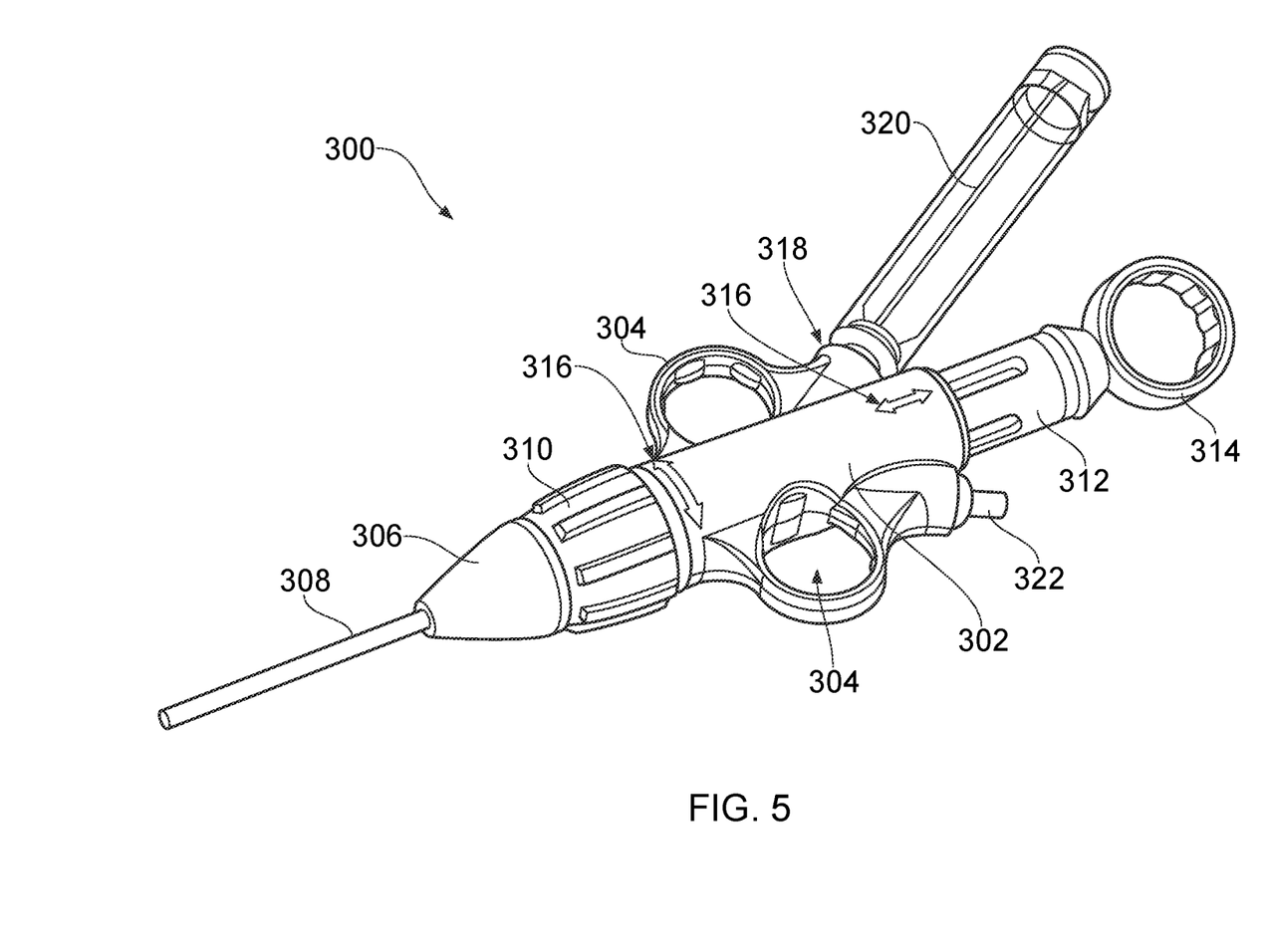
FIG. 5 is a perspective view of an interface joint that is a second embodiment of the invention.

FIG. 5 is a perspective view of an interface joint 300 that is a second embodiment of the invention. The interface joint 300 comprise a housing 302. The interface joint 300 may be used with the apparatus 100 discussed above, in place of the interface joint 106 and torque transfer unit 116.

The housing 302 may be a rigid hollow casing that encloses the junctions and components discussed below. The casing may be made from moulded plastic, e.g. in two halves that are securable together, e.g. by welding or the like.

The housing 302 has a pair of ring elements 304 integrally formed on opposing sides thereof. The ring elements 304 provide finger grips for a user operating the device.

The housing 302 has a outlet port at a distal end thereof. A flexible shaft 308 extends out of the output port, whereupon it may be fed into an instrument channel of a surgical scoping device. The distal end of the housing may comprise a conical tip section 306. The tip section may be rigid. Alternatively it may be deformable e.g. to provide strain relief for the flexible shaft 308.

A collar 310 is rotatable mounted on a distal portion of the housing 302. The collar 310 is operably coupled to the flexible shaft 308 whereby rotation of the collar 310 relative to the housing 302 causes the flexible shaft to rotate. This rotation may be transferred through the instrument channel to cause rotation of an electrosurgical instrument at a distal end of the flexible shaft 308 relative to the instrument channel. The collar 310 may be arranged to rotate about an axis that is aligned with the flexible shaft as it leaves the housing 302. This ensures that the rotation of the collar 310 is intuitively linked to the resulting rotation of the instrument tip. The collar 310 may have a plurality of upstanding ridges to facilitate grip.

The housing 302 may include a feedback mechanism for a user to sense the degree of rotation being applied. The feedback mechanism may be haptic or audio. For example, the housing 302 and collar 310 may have interengaging elements that produce a sound (e.g. a click) or a impulse that can be perceived by the user to give feedback on the incremental degrees of rotation being applied.

The housing 302 has three ports at a proximal end thereof.

A first proximal port is in line with (i.e. is coaxial with) the output port. The first port receives a slider element 312 which is movable relative to the housing in a longitudinal direction. The slider element is connected to a needle actuation rod (not shown) that passes through the flexible shaft to control deployment and retraction of a needle in the electrosurgical instrument in a similar manner to that discussed above with respect to FIGS. 2 to 4. The housing 302 may comprise a guide track (not shown) that defines the longitudinal path of motion for the slider element 312. The slider element may have a proximal finger grip 314, e.g. a ring for receiving a user's thumb in this example, for ease of deployment.

One or more biasing elements (e.g. springs or other resilient structures) may be provided between the housing 302 and the slider element 312 to urge the needle actuation mechanism into a certain configuration, e.g. a retracted configuration.

Markings 316 may be formed on the housing to indicate the direction of movement of the collar 310 and the slider element 312.

A second proximal port 318 is for receiving a fluid supply. In FIG. 5, the second proximal port 318 is connected to a syringe body 320, e.g. for injecting a liquid such as saline or hyaluronic acid.

A third proximal port is for receiving power from the electrosurgical generator. The third proximal port may have a connector 322, e.g. a QMA connector or the like, arranged to connect to a coaxial cable from the electrosurgical generator.

The second and third proximal ports may be on opposite sides of the first proximal port, and may be angled away from it, e.g. to facilitate attachment of the corresponding components.

The housing 300 operates in a similar manner to housing 200 discussed above. Inputs from the fluid supply, needle actuation mechanism and power supply are combined together and conveyed through a passageway formed in the flexible shaft 308.

Figure 6:
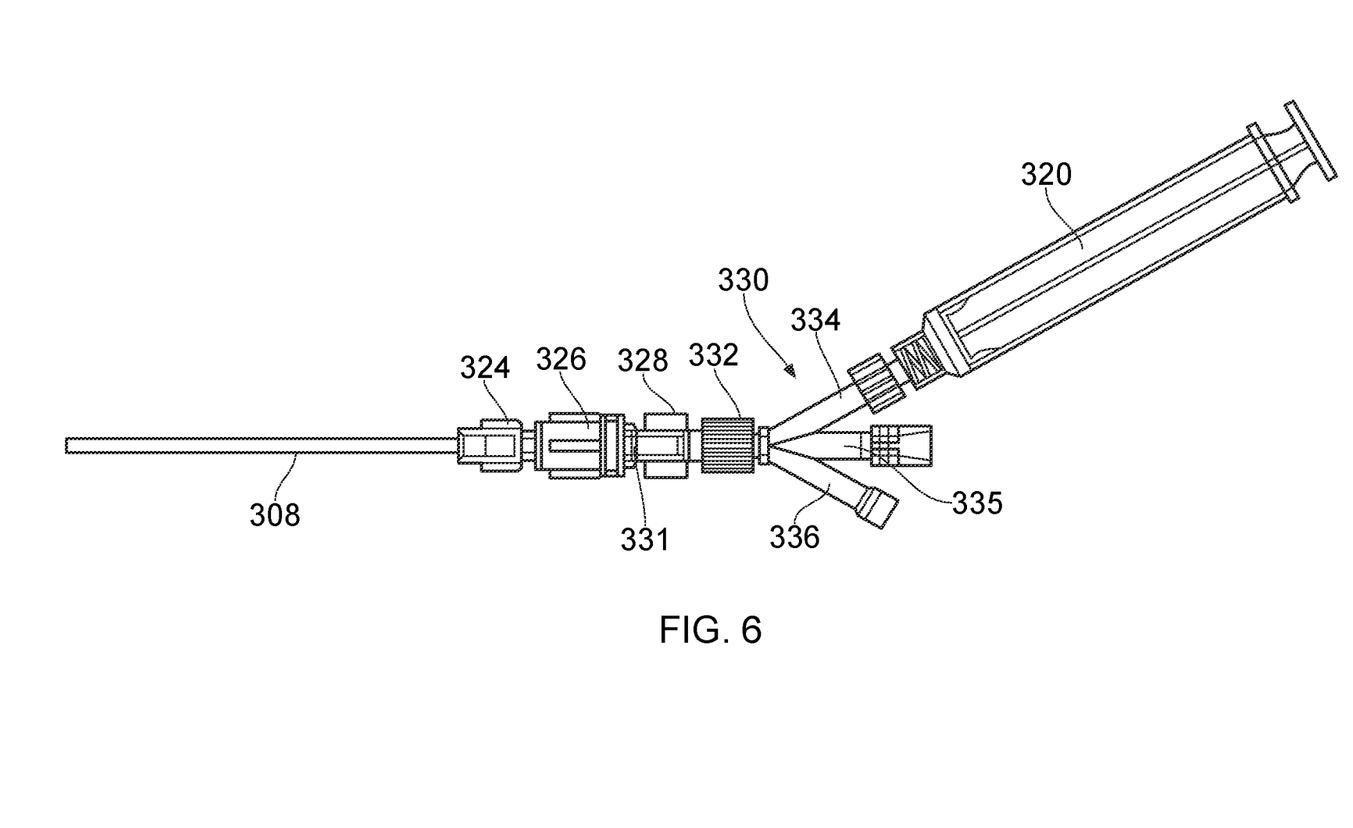
FIG. 6 is a side view of the internal components of the interface joint of FIG. 5.

FIG. 6 is a side view of the internal components of the interface joint 300. The backbone of the interface joint 300 comprises a branched conduit connector 330 and a main conduit 331. The branched conduit connector 330 may resemble a tri-connector conduit junction, having a three angled inlet ports 334, 335, 336 in fluid communication with an outlet port that is connected to the main conduit 331 by a suitable fluid tight coupling 332. The main conduit 331 may define a longitudinal passageway that is in fluid communication with the passage within the flexible shaft 308. The main conduit 331 may be aligned along the axis of the flexible shaft 308 as it leave the housing.

The flexible shaft 308 is secured to an output portion 324 of a rotatable luer lock fitting 326, which is mounted on the distal end of the main conduit 331. The flexible shaft 308 may be secured or potted within the output portion in a fluid tight manner, e.g. using a suitable adhesive.

The rotatable luer lock fitting 326 may be operably connected to the collar 310 such that rotation of the collar causes the rotatable luer lock fitting 326 to rotate about the main conduit 331, which in turn causes the flexible shaft 308 to rotate relative to the housing 302. Rotation of the main conduit 331 is prevent by ensuring that is fixed to the housing 302 in a non-rotatable manner. For example, a retaining element 328 may be mounted on the main conduit to secure it within the housing 302.

The inlet ports 334, 335, 336 of the branched conduit connector 330 provide the first, second and third ports discussed above. Thus, a first inlet port 334 is connected to the fluid supply (e.g. a syringe housing 320). A second inlet port 335 receives the needle actuation rod (not shown). A third inlet port 336 receives the coaxial cable from the electrosurgical generator. The second port 335 and third ports 336 may include plugs (not shown) for prevent leakage of fluid received through the first inlet port 334 in a similar manner to that shown in FIGS. 2 to 4 above.

Fluid from the first inlet port 334, a needle actuation rod (not shown) from the second inlet port 335, and a coaxial transmission line (not shown) from the third inlet port are combined within and conveyed by the main conduit 331 to the passage within the flexible shaft 308.

An advantage of this arrangement is that both the shaft rotation mechanism (which controls turning of the instrument) and the needle actuation instrument are provided on the same unit.

Figure 7:
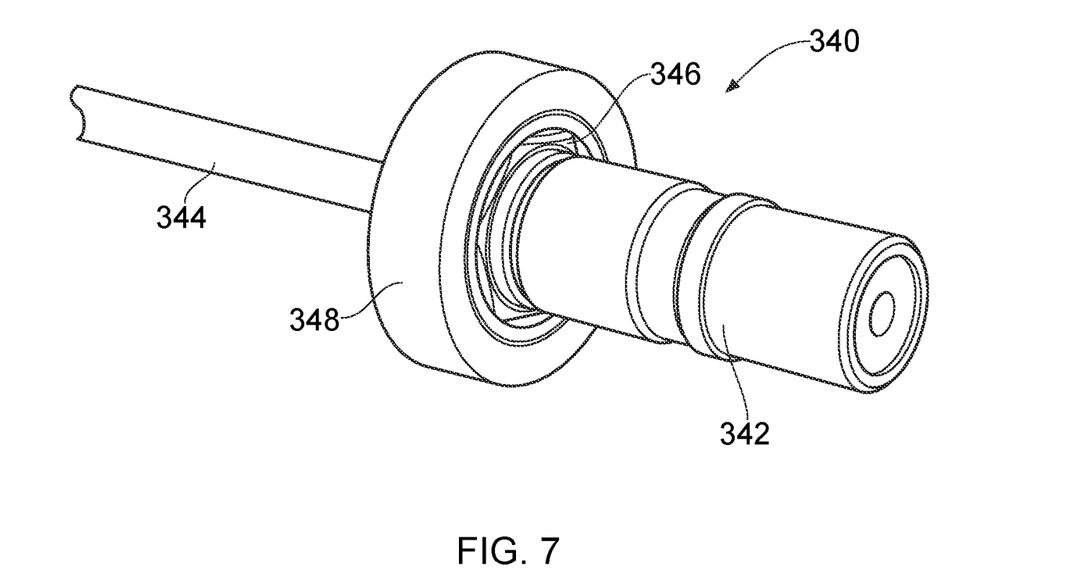
FIG. 7 is a perspective view of a rotatable connection interface suitable for used with the interface joint of FIG. 5.

FIG. 7 is a perspective view of a rotatable power connection interface 340 that can be used at the third port 336 of the branched conduit connecter 330 of FIG. 6. The rotatable connection interface 340 comprises a coaxial cable connector 342 (e.g. a QMA connector) having a distal head portion 346 mounted within a bearing unit 348 which is securable to the housing of an interface joint such as that discussed above, e.g. within the third port 336 of the branched conduit connecter 330. The a coaxial cable connector 342 is arranged to connect a coaxial cable from the electrosurgical generator with a coaxial transmission line 344 within the housing. Since the coaxial transmission line 344 is connected to the electrosurgical instrument, it will rotate with the flexible shaft when the shaft is turned, e.g. by operating the collar 310 discussed above. The bearing unit 348 may be a ball bearing or the like that permits free rotation of the connector 342 relative to the housing. This can prevent tension from accumulating in the coaxial transmission line 344, and may reduce resistance caused by components within the flexible shaft.

The invention claimed is:

1. An interface joint for interconnecting an electrosurgical generator and an electrosurgical instrument, the interface joint comprising:
    a housing made of electrically insulating material, the housing having:
        a first inlet for receiving radiofrequency (RF) electromagnetic (EM) energy and/or microwave frequency EM energy from the electrosurgical generator,
        a second inlet for receiving fluid, and
        an outlet;
    a flexible shaft for connecting the housing to the electrosurgical instrument, the flexible shaft extending through the outlet and having a longitudinal passage therein, which provides a fluid flow path that is in fluid communication with the second inlet, and which conveys a coaxial transmission line that is connected to the first inlet;
    an actuation mechanism operably connected to the electrosurgical instrument to control deployment of a fluid delivery structure, the actuation mechanism comprising:
        an actuation rod extending out of the housing through the outlet,
        an actuator movably mounted on the housing and connected to the actuation rod; and
    a shaft rotation mechanism for rotating the flexible shaft relative to the housing, the shaft rotation mechanism comprising a rotation actuator rotatably mounted on the housing and operably coupled to the flexible shaft;
    wherein the housing includes an internal watertight branched conduit that provides the fluid flow path between the second inlet and the outlet, the branched conduit comprising:
        a main conduit fixed to the housing, and
        a rotating luer lock fitting rotatably mounted to a distal end of the main conduit,
    wherein the flexible shaft is non-rotatably coupled to the rotating luer lock fitting, and
    wherein the rotation actuator is operable to rotate the rotating luer lock fitting relative to the main conduit.

2. The interface joint according to claim 1, wherein the actuation rod extends through the longitudinal passage of the flexible shaft.

3. The interface joint according to claim 1, wherein the rotation actuator comprises a collar mounted around a distal portion of the housing.

4. The interface joint according to claim 1, wherein the rotation actuator is rotatable relative to the housing around an axis that is aligned with a direction in which the flexible shaft passes through the outlet.

5. The interface joint according to claim 1, wherein the branched conduit has a first port adjacent to the first inlet for admitting a coaxial cable.

6. The interface joint according to claim 5, wherein the first port comprises a plug which defines a watertight passage for a coaxial cable.

7. The interface joint according to claim 5, wherein the branched conduit defines a second port adjacent the actuation mechanism for admitting the actuation rod.

8. The interface joint according to claim 7, wherein the second port comprises a plug which defines a watertight passage for the actuation rod.

9. The interface joint according to claim 1 having a connector rotatably mounted at the first inlet, wherein the connector is arranged to connect to a coaxial cable.

10. The interface joint according to claim 9, wherein the connector is mounted within a bearing unit that is fixed to the housing.

11. The interface joint according to claim 1, wherein a distal end of the actuation rod is connected to a proximal end of a needle ferrule, which has an internal volume in fluid communication with the fluid flow path through the flexible shaft, and wherein a needle is mounted in the distal end of the needle ferrule, the needle being in fluid communication with the internal volume.

* * * * *

UNITED STATES PATENT AND TRADEMARK OFFICE
CERTIFICATE OF CORRECTION

PATENT NO. : 11,980,413 B2
APPLICATION NO. : 17/685851
DATED : May 14, 2024
INVENTOR(S) : Christopher Paul Hancock et al.

It is certified that error appears in the above-identified patent and that said Letters Patent is hereby corrected as shown below:

On the Title Page

Item (73), Assignee, please delete "Monmouth" and insert therefor -- Chepstow, Monmouthshire --.

Signed and Sealed this
Second Day of July, 2024

Katherine Kelly Vidal
Director of the United States Patent and Trademark Office